United States Patent [19]
Vari et al.

[11] Patent Number: 5,456,252
[45] Date of Patent: Oct. 10, 1995

[54] INDUCED FLUORESCENCE SPECTROSCOPY BLOOD PERFUSION AND PH MONITOR AND METHOD

[75] Inventors: Sandor G. Vari, Encino, Calif.; Theodore Papazoglou, Heraklion, Greece; Warren S. Grundfest, Los Angeles, Calif.

[73] Assignee: Cedars-Sinai Medical Center, Los Angeles, Calif.

[21] Appl. No.: 129,406

[22] Filed: Sep. 30, 1993

[51] Int. Cl.⁶ ..................................................... A61B 6/00
[52] U.S. Cl. ........................... 128/633; 128/634; 128/665; 128/666
[58] Field of Search ..................... 128/633, 634, 128/664, 665, 666; 356/326, 328

[56] References Cited

U.S. PATENT DOCUMENTS

| | | | |
|---|---|---|---|
| 3,313,290 | 8/1963 | Chance et al. | 128/2 |
| 3,706,612 | 10/1971 | Clemens | 356/178 |
| 3,807,862 | 4/1974 | Hatzenbuhler . | |
| 3,830,222 | 8/1974 | Chance | 128/2 A |
| 3,975,098 | 8/1976 | West | 356/85 |
| 4,031,398 | 6/1977 | Callis et al. . | |
| 4,162,405 | 7/1979 | Chance et al. | 350/461 B |
| 4,170,987 | 10/1979 | Anselmo et al. | 128/665 |
| 4,178,917 | 12/1979 | Shapiro | 128/665 |
| 4,184,175 | 1/1980 | Mullane, Jr. | 358/93 |
| 4,236,526 | 12/1980 | Richard | 128/633 |
| 4,412,543 | 11/1983 | Vassiliadis et al. | 128/633 |
| 4,449,535 | 5/1984 | Renault | 128/634 |
| 4,479,499 | 10/1984 | Alfano | 128/665 |
| 4,569,354 | 2/1986 | Shapiro et al. | 128/665 |
| 4,608,990 | 9/1986 | Elings | 128/633 |
| 4,629,693 | 12/1986 | Khanna | 435/7 |
| 4,631,413 | 12/1986 | Jensen et al. | 250/458.1 |
| 4,675,529 | 6/1987 | Kushida | 250/458.1 |
| 4,678,277 | 7/1987 | Delhaye et al. . | |
| 4,894,547 | 1/1990 | Leffell et al. | 250/461.2 |

(List continued on next page.)

OTHER PUBLICATIONS

Pini et al., "Laser Dentistry: Root Canal Diagnostic Technique Based on Ultraviolet-Induced Fluorescence Spectroscopy," Lasers in Surgery and Medicine, vol. 9, pp. 358–361 (1989).

Mendelson, et al., "Blood Glucose Measurement by Multiple Attenuated Total Reflection and Infrared Absorbtion," IEEE Trans. on Biomed. Eng., vol. 37, No. 5, May 1990, pp. 458–464.

(List continued on next page.)

*Primary Examiner*—Ruth S. Smith
*Attorney, Agent, or Firm*—Pretty, Schroeder, Brueggemann & Clark

[57] ABSTRACT

A medical monitor, and related method, determines a pre-existing physiological property of an organ of a patient by monitoring fluorescent light produced by constituents associated with the metabolic and structural condition of the organ. The monitor illuminates the organ with ultraviolet excitation light that induces some constituents of the organ to fluoresce, with the fluorescent light being monitored and processed to determine pre-existing physiological properties of the organ. A sensor monitors the return light, which includes fluorescent light produced by the fluorescent constituents of the organ, and generates first and second electrical signals indicative of the intensity of light at two wavelength. One wavelength is associated with the fluorescence of collagen, a constituent associated with organ's structural properties, and the other wavelength is a associated with the fluorescence of NADH, a constituent associated with the organ's metabolism. A processor then processes the first and second electrical signals to determine the localized pH of the organ. A fiber-optic waveguide is used to guide the excitation light from the laser light source to the organ and the return light from the organ to the sensor. In another aspect of the invention, the sensor generates a third electrical signal associated with the fluorescence of elastin, a constituent associated with the organ's structural properties. The processor processes the first, second and third electrical signals to determine the perfusion or oxygenation of the organ.

37 Claims, 7 Drawing Sheets

U.S. PATENT DOCUMENTS

| | | | |
|---|---|---|---|
| 4,930,516 | 6/1990 | Alfano et al. | 128/665 |
| 4,951,669 | 8/1990 | Maxwell et al. | 128/637 |
| 4,957,114 | 9/1990 | Zeng et al. | 128/665 |
| 4,981,138 | 1/1991 | Deckelbaum et al. | 128/665 |
| 4,981,779 | 1/1991 | Wagner | 435/288 |
| 5,001,054 | 5/1991 | Wagner | 435/14 |
| 5,014,707 | 5/1991 | Schwartz | 128/633 |
| 5,034,189 | 7/1991 | Cox et al. | 422/52 |
| 5,037,200 | 8/1991 | Kodama . | |
| 5,037,738 | 8/1991 | Lamos et al. | 435/12 |
| 5,042,494 | 8/1991 | Alfano | 128/665 |
| 5,046,501 | 10/1991 | Crilly | 128/665 |
| 5,072,373 | 12/1991 | Taratuta et al. | 128/633 |
| 5,074,306 | 12/1991 | Green et al. | 128/664 |
| 5,093,266 | 3/1992 | Leader et al. | 436/68 |
| 5,115,137 | 5/1992 | Jeffcoat et al. | 128/634 |
| 5,127,405 | 7/1992 | Alcala et al. | 128/633 |
| 5,172,693 | 12/1992 | Doody | 128/633 |
| 5,209,231 | 5/1993 | Cote et al. | 128/633 |
| 5,212,099 | 5/1993 | Marcus . | |
| 5,217,456 | 8/1993 | Narcisco, Jr. | 606/15 |
| 5,243,983 | 9/1993 | Tarr et al. . | |
| 5,280,788 | 1/1994 | Janes et al. . | |
| 5,341,805 | 8/1994 | Stavridi et al. | 128/633 |
| 5,348,018 | 9/1994 | Alfano . | |

OTHER PUBLICATIONS

Willenborg, "Dental Laser Applications: Emerging to Maturity," Lasers in Surgery and Medicine, vol. 9, pp. 309–313 (1989).

"Substance Identification Neural Network," Physical Optical Corp. product information, Date: unknown.

Bassnett et al., "Intracellular pH measurement using single excitation–dual emission fluorescence ratios," Am. J. Physiol. 258, 1990, pp. C171–C178.

Ring et al., "In–Vitro Evaluation of New Fiber Optic pH, Carbon Dioxide, and Oxygen Sensor Systems," Date: unknown, 10 pgs.

Ring et al., "In–Vitro Evaluation of New Fiber Optic pH, Carbon Dioxide and Oxygen Sensor Systems," SPIE OE LASER '92, Conf. 1648, Jan. 1992, 11 pgs.

Green et al., "Burn Depth Estimation Using Indocyanine Green Fluorescence Arch Dermatol," vo. 128, Jan. 1992, pp. 43–49.

Moneta et al., "Infrared Fluorescence Videomicroscopy of Sking Capillarie With Indocynine Green," Int. J. Microcirc. Clin. Exp., pp. 25–34, (1987).

Gotti et al., "Evaluation of the Burn Wound with Perfusion Fluorometry," J. Trauma Vo. 23, No. 3, Mar. 1983, pp. 202–206.

Afromowitz et al., "Multispectral Imaging of Burns Wounds," IEEE Trans. Biomed. Eng., Vo. 35, No. 10, Oct. 1988, pp. 842–849.

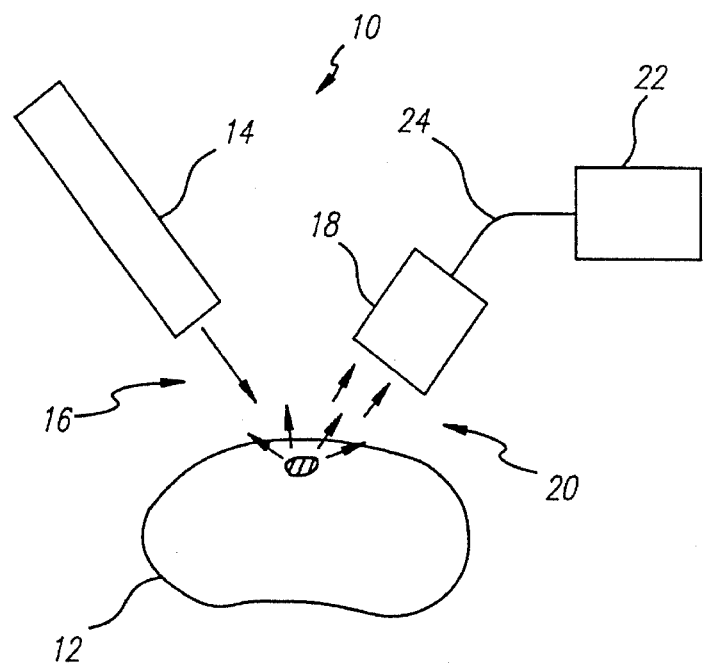
FIG. 1
FIG. 2A
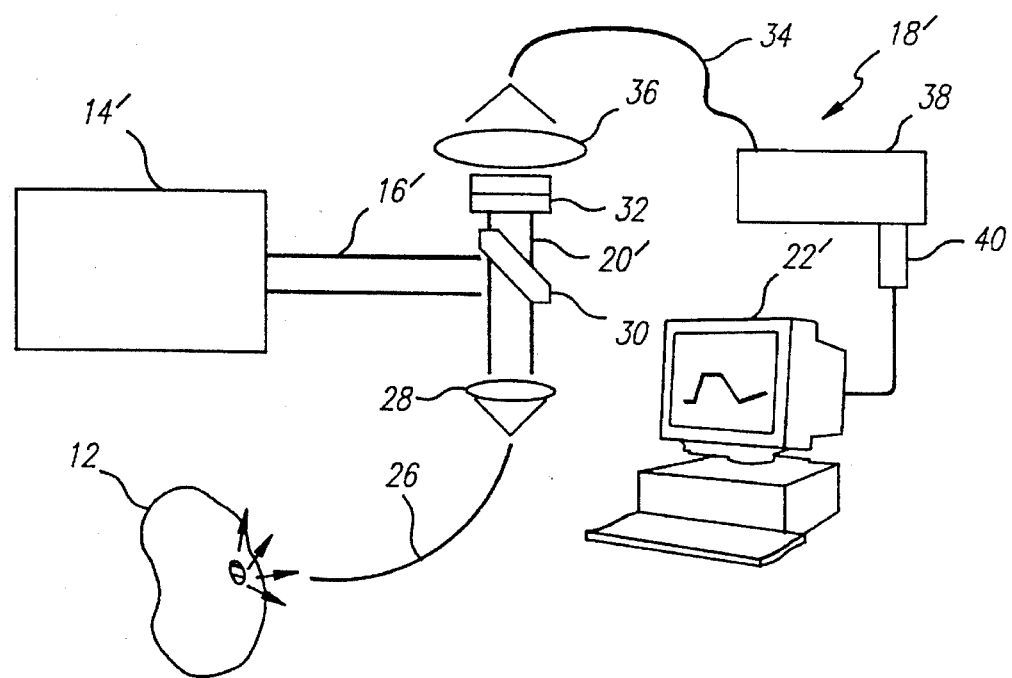

INDUCED FLUORESCENCE SPECTROSCOPY BLOOD PERFUSION AND PH MONITOR AND METHOD

BACKGROUND OF THE INVENTION

This invention relates generally to physiological monitors and, more particularly, to blood perfusion and pH monitors that determine the oxygenation and acidity or alkalinity in a patient's vital organs and tissues by means of induced fluorescence spectroscopy.

Early warning of the deterioration in a patient's condition largely determines the effectiveness of life sustaining critical care treatment. Tissue perfusion and oxidative metabolism may be compromised in critically ill patients in a number of pathological situations and disease states such as hemorrhage, hypoxia, septic shock, etc. This compromise often results in the redistribution of the blood flow within a patient's body which favors the brain and the heart at the expense of the skeletal muscles, kidneys and the splanchnic organs. Reduced perfusion and oxygen availability at the level of these organs may lead to ischemia which may cause tissue injury and organ failure. Also, certain conditions may lead to acidosis or alkalosis. The pH of body fluids must be maintained very near 7.4 (close to neutrality) for the body's metabolic reactions to proceed properly. Acidosis occurs if the pH falls below 7.3.

Currently, clinical techniques to monitor oxygen delivery and pH in the body rely on global metabolic measurements. Such global measurement techniques are generally unsuited for early detection and continuous monitoring of local deficiencies such as the lack of oxygen delivered to an organ.

Fluorescence spectroscopy techniques have been developed for measuring the heterogeneity of oxygen delivery to organs. Such techniques typical involve the measurement of a chemical, such as NADH, that is associated with the metabolic state of the organ. Such techniques are not widely used clinically. One reason for such limited use is the desirability of calibrating or compensating for measurement variations caused by equipment variations or the like. Such compensation typically requires careful optical splitting of the fluorescence excitation light to provide a reference light signal of known relative intensity with respect to the excitation light.

From the discussion above, it should be apparent that there is a need for a physiological medical monitor that is relatively immune to equipment variations or the like, that is simple and rapid to use, and that provides immediate results regarding a patients metabolic state. The present invention addresses these needs.

SUMMARY OF THE INVENTION

The present invention is embodied in a medical monitor, and related method, that determines the metabolic state of an organ by monitoring fluorescent light produced directly by the organ's tissues. The monitor illuminates the organ with excitation light that induces the metabolic and structural constituents of the organ to fluoresce, with the fluorescent light being detected and processed to determine the organ's physiological properties or condition.

The monitor includes a light source, a sensor, and a processor. The light source emits excitation light that is directed at the organ to induce the constituents of the organ to fluoresce. The excitation light causes the organ to produce return light, which includes fluorescent light produced by the organ's metabolic constituents, which include NADH, and structural constituents, which include collagen and elastin. The sensor monitors the return light and generates a plurality of signals representing the intensity of light at predetermined wavelengths or within predetermined wavelength bands. A first signal is indicative of the intensity of return light having a wavelength associated with the fluorescence of NADH. A second signal is indicative of the intensity of return light having a wavelength associated with the fluorescence of collagen. The processor processes the electrical signals to determine the physiological condition of the organ. The processor may include an artificial neural network.

In a more detailed feature of the invention, the light source emits excitation light having a wavelength between about 250 nanometers and about 450 nanometers. A typical narrowband ultraviolet light source is an excimer laser having a wavelength of about 308 nanometers. The wavelength associated with the collagen fluorescence is about 100 nanometers longer than the wavelength of the excitation light. Using an excimer laser, the wavelength associated with the collagen fluorescence is about 410 nanometers. Likewise, the wavelength associated with the NADH fluorescence is about 190 nanometers longer than the wavelength of the excitation light. Using an excimer laser, the wavelength associated with the NADH fluorescence is centered at about 495 nanometers.

The processor determines a ratio of the light-intensities for the predetermined wavelength bands. The pH of the organ is determined from the ratio of the light intensities. The algebraic formula for the ratio is as follows:

$$R_{pH} = I^{NADH}/I^{COLLAGEN}$$

In another more detailed feature of the invention, the sensor generates a third signal associated with the intensity of return light having a wavelength associated the fluorescence of elastin. The wavelength associated with the elastin fluorescence is about 70 nanometers longer than the wavelength associated with the wavelength of the excitation light. Using an excimer laser, the elastin fluorescence is centered at about 375 nanometers. The processor determines the perfusion of the organ using the following formula:

$$R_{PERFUSION} = (I^{ELASTIN} - I^{COLLAGEN})/(I^{NADH} - I^{COLLAGEN})$$

In another more detailed feature of the invention, the sensor has more than one detector that simultaneously monitors the return light within the first and second wavelength band. One of the detectors determines the intensity of light within the first wavelength band and the another detector determines the intensity of light within the second wavelength band. Each detector provides a signal indicative of the intensity of light within the corresponding wavelength band. Further, a third detector may be included which determines the intensity of light within the third wavelength band and produces a signal indicative of that intensity.

In another more detailed feature of the invention, the sensor includes a dichroic filter used to separate the excitation light from the return light, a stop having a slit, and a grating used to separate the turn light into its spectral wavelengths. The sensor may include a spectrograph having a detector array which is connected to an optical analyzer.

In another more detailed feature of the invention, a waveguide is used to guide the excitation light from the light source to the sample. The same waveguide or another waveguide is used to guide the return light from the sample to the sensor. If fiber-optic waveguides are used, they may be held together in a bundle for ease of use.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a block diagram of a physiology monitoring system embodying the invention.

FIGS. 2A and 2B are block diagrams of embodiments of a physiology monitoring system of FIG. 1 which use one or more fiber-optic waveguides to transmit and collect light.

DESCRIPTION OF THE PREFERRED EMBODIMENTS

Figure 13:
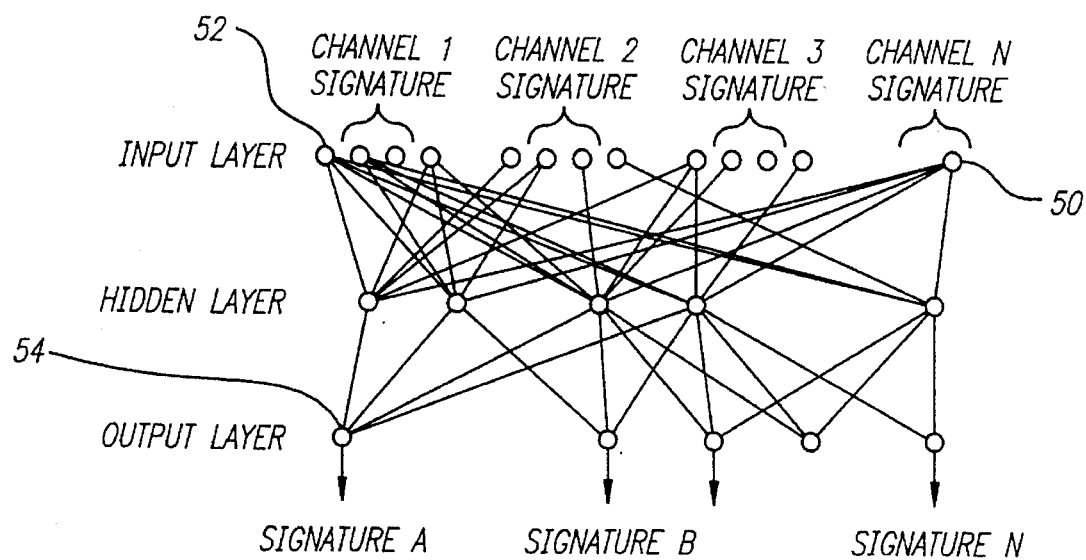
FIG. 13 is a schematic diagram of the concept of a neural network.

As shown in the exemplary drawings, the present invention is embodied in a physiology monitoring system 10, and related method, for determining the metabolic state of an organ 12 by directly monitoring the fluorescence of several compounds within the organ without the use of injected fluorescent dyes or the like. More specifically, the physiology monitoring system uses induced fluorescence spectroscopy to monitor the relative pH and blood perfusion of the organ by inducing the organ's metabolic and structural compounds to fluoresce and by detecting the intensity of the fluorescence. Also, the fluorescence spectroscopy monitoring system uses relatively inexpensive instrumentation and enhances resolution in comparison to prior optical spectroscopy methods. The fluorescence spectroscopy monitoring system is relatively noninvasive, gives immediate results and is easily adapted to most laboratory and clinical units.

In the monitoring system 10 shown in FIG. 1, a light source 14 directs ultraviolet or blue excitation light 16 at the organ 12, to induce the organ's tissues to fluoresce. A sensor 18 monitors return light 20 from the organ, such return light including any tissue fluorescence, and generates a plurality of electrical signals associated with the intensity of return light within predetermined wavelength bands associated with metabolic and structural constituents within the organ. The plurality of electrical signals are communicated from the sensor to a processor 22 by means of data path 24. The processor then processes the plurality of electrical signals to determine a physiological property or condition of the tissues.

The light source 14 is also referred to as the excitation source. The excitation light 16 from the light source typically has a wavelength between 250 nanometers to 450 nanometers. The excitation light can be produced from any type of ultraviolet or blue light source. In the preferred embodiment, the light source is an ultraviolet excimer laser having a wavelength of about 308 nm and an energy density of about 2 to 5 millijoules per square millimeter. Alternatively, a nitrogen laser, a helium—cadmium laser, a frequency-multiplied diode laser, a solid-state laser, an arc lamp or a light-emitting diode (LED) can be used for the light source. The intensity or energy density of the excitation light is typically between one millijoule per square millimeter and 15 millijoules per square millimeter. However, as will be appreciated, care must be taken to insure that the energy density is not too high or too low. If the energy density is too high, ablation of the tissue can occur, whereas, if the energy density is too low, obtaining a sufficient electrical signal can be difficult.

The detectors in the sensor 18 can be as simple as individual light-sensitive diodes, with appropriate bandpass filters, or more complicated such as an optical spectrum analyzer that analyzes a broad spectrum of the return light. Preferably, the sensor is a suitable optical spectrometer having a detector array which is used to monitor a variety of wavelengths as desired with each individual array element monitoring a specific wavelength region. A suitable optical spectrometer is a SPEX 500M available from SPEX Industries, Inc. of Edison, N.J. A suitable array detector is a Model 1420 or 1421 intensified silicon photodiode array detector available from EG&G Princeton Applied Research of Princeton, N.Y.

In its simplest form, the processor 22 receives the electrical signals from the sensor 18 and algebraically manipulates and combines the signals to determine and indicate the current physiological condition of the organ's tissues.

The process of determining the physiological state of the organ's tissues is better understood with reference to the graphs shown in FIGS. 3–12. These graphs indicate the results of experiments performed on the organs of anesthetized rabbits.

Figure 3:
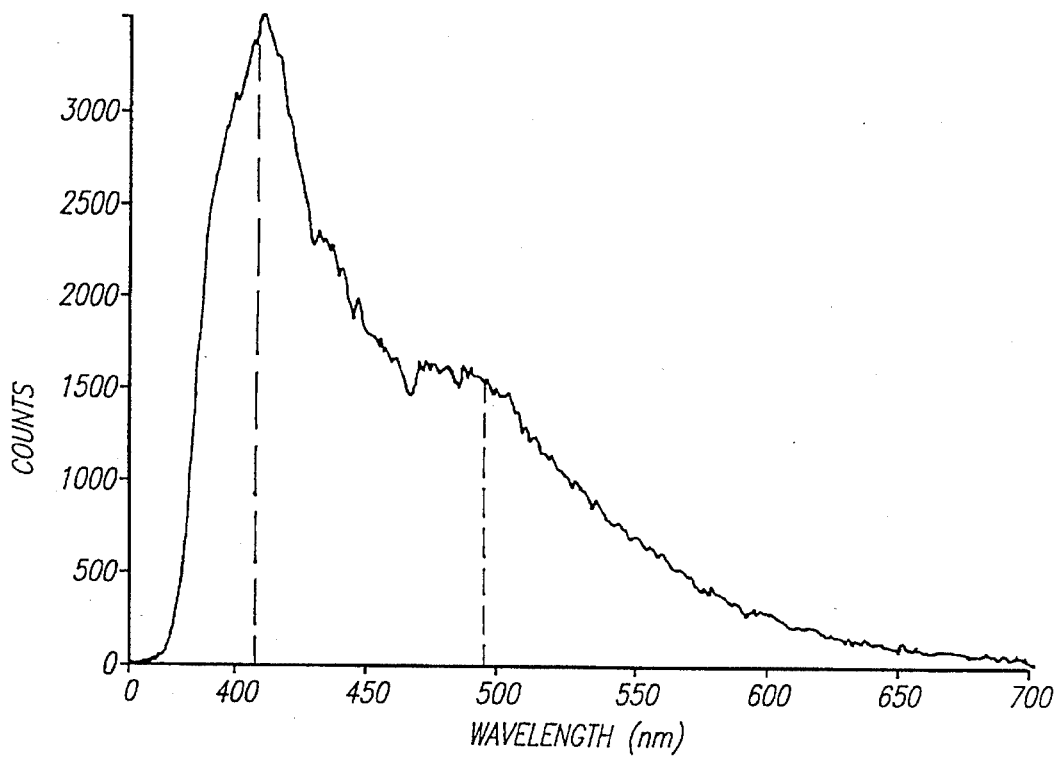
FIG. 3 is a graph of the intensity of fluorescence versus wavelength for a kidney having a blood pH of 7.21–7.40 induced to fluoresce by laser light having a wavelength of about 308 nanometers.

The fluorescence spectrum shown in FIG. 3 is that of a rabbit's kidney after excitation with an ultraviolet excimer laser light having a wavelength of about 308 nanometers. The kidney has a pH between 7.21 and 7.40. Two wavelengths of the spectrum are highlighted in FIG. 3. One wavelength, which is closely associated with the fluorescence of collagen, is centered at approximately 410 nanometers, and the other wavelength, which is closely associated with the fluorescence of NADH, is centered at approximately 495 nanometers. Collagen is a protein that occurs as a chief constituent of connective tissue fibrils. As part of the tissue's structure, the amount of collagen in the tissue's structure varies relatively slowly over time. NADH is an important constituent of the organ and is an agent in the metabolism of the tissue's cells and varies relatively quickly over time and provides an indication of the acidity or alkalinity of the tissues.

Figure 4:
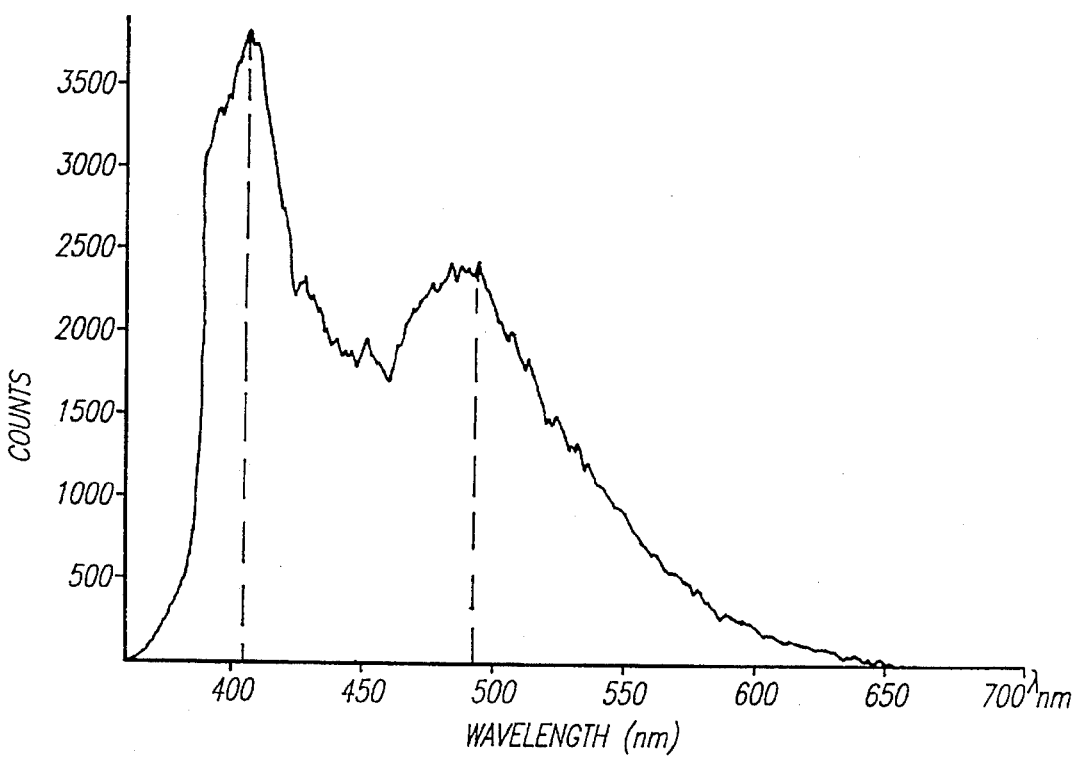
FIG. 4 is a graph of the intensity of fluorescence versus wavelength for a kidney having a blood pH of 7.01–7.20 induced to fluoresce by laser light having a wavelength of about 308 nanometers.

By calculating the ratio of the intensity of light at the NADH peak to the intensity of light at the collagen peak, a relative determination of the pH of the organ's tissues can be determined. The pH of the kidney in FIG. 3 is known to be between 7.21 and 7.40. The pH of the kidney shown in FIG. 4 is known to be between 7.01 and 7.20. The pH of the kidney shown in FIG. 5 is known to be between 6.80 and 7.00.

Figure 5:
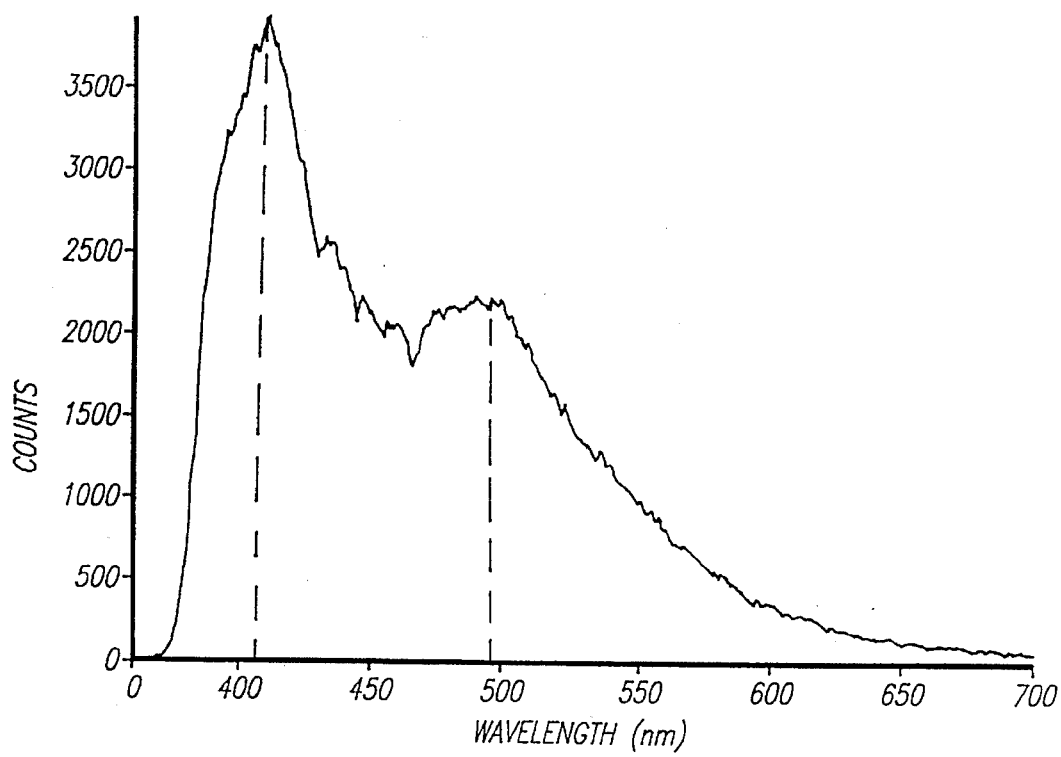
FIG. 5 is a graph of the intensity of fluorescence verses wavelength when a kidney having a blood pH of 6.80–7.00 induced to fluoresce by laser light having a wavelength of about 308 nanometers.

As can be seen in FIGS. 3–5, the profile of the fluorescence spectrum changes as the pH changes. The differences can be quantified by calculating the following formula:

$$R_{pH} = I^{NADH}/I^{COLLAGEN}$$

where $I^{NADH}$ is the intensity of light associated with the fluorescence of NADH and $I^{COLLAGEN}$ is the intensity of light associated with the fluorescence of collagen. The following ratios were calculated from measurement performed on a large number of rabbits:

| pH | R |
| --- | --- |
| 7.21–7.40 | 0.625 +/– 0.128 |
| 7.01–7.20 | 0.686 +/– 0.209 |
| 6.80–7.00 | 0.752 +/– 0.233 |

Using simple linear regression, the mean slope of the ratios was calculated to be –0.203 and the standard deviation was calculated to be –0.136. The ratio (R) for the graphs in FIGS. 3–5 appear to be 0.429, 0.608 and 0.613, respectively.

Figure 6:
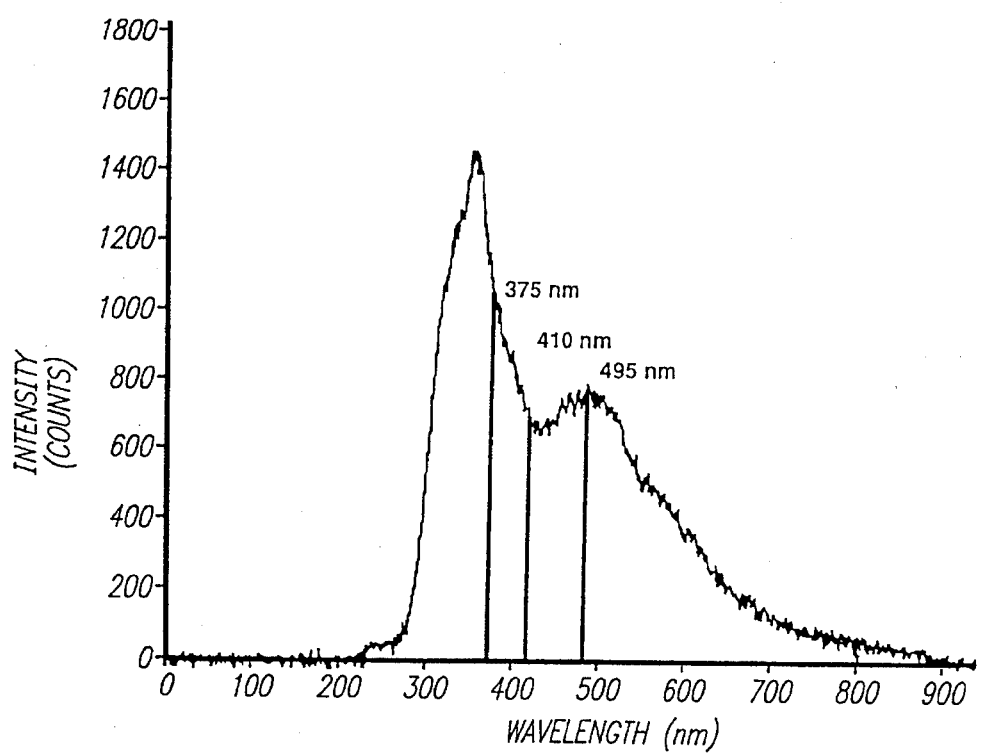
FIG. 6 is a graph of the intensity of fluorescence verses wavelength of a fully perfused kidney induced to fluoresce by laser light having a wavelength of about 308 nanometers.

The blood perfusion of an organ is similarly detected using induced fluorescence spectroscopy. The fluorescence spectrum shown in FIG. 6 is the fluorescence spectrum of a fully perfused kidney after excitation with an ultraviolet excimer laser having a wavelength of 308 nanometers. Three wavelengths are highlighted on the graph. Two of the highlighted wavelengths are associated with the fluorescence of collagen and NADH as discussed above. The third wavelength, which is closely associated with the fluorescence of elastin, is at approximately 375 nanometers. Elastin is a protein that is similar to collagen and is the chief constituent of elastic fibers. As part of the tissue's structure, the amount of elastin in the tissue also varies relatively slowly with respect to the metabolic agent NADH.

Figure 7:
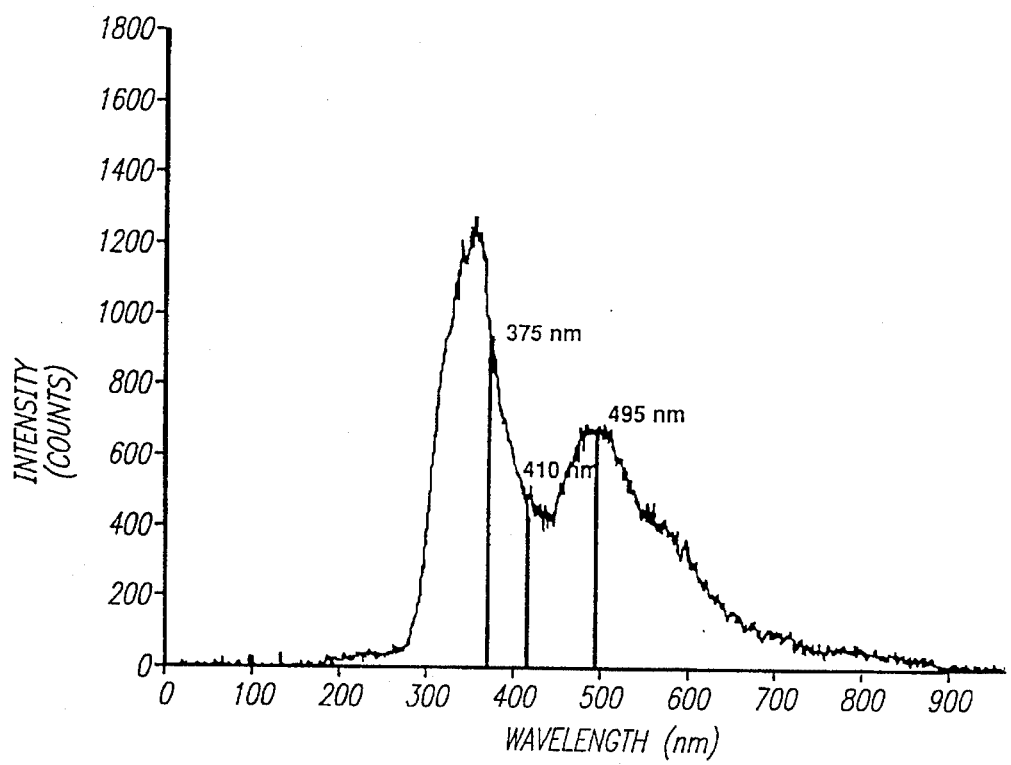
FIG. 7 is a graph of the intensity of fluorescence verses wavelength of a kidney having its blood perfusion reduced by 35% of the normal blood flow induced to fluoresce by laser light having a wavelength of about 308 nanometers.
Figure 8:
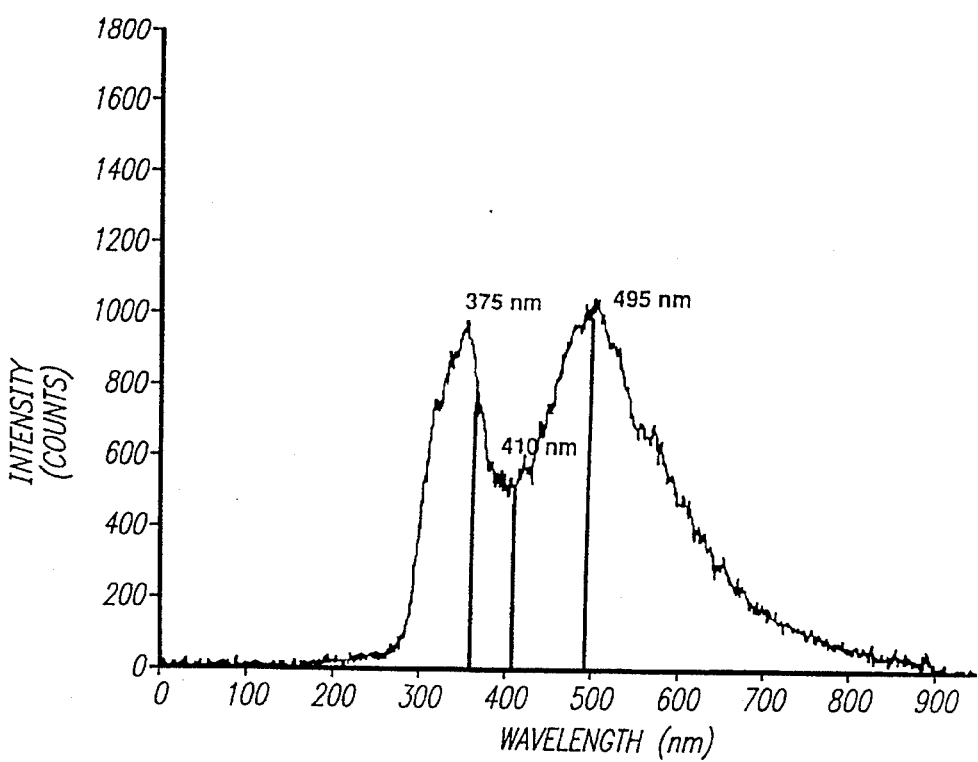
FIG. 8 is a graph of the intensity of fluorescence verses wavelength of a kidney having its blood perfusion reduced by 70% of the normal blood flow induced to fluoresce by laser light having a wavelength of about 308 nanometers.
Figure 9:
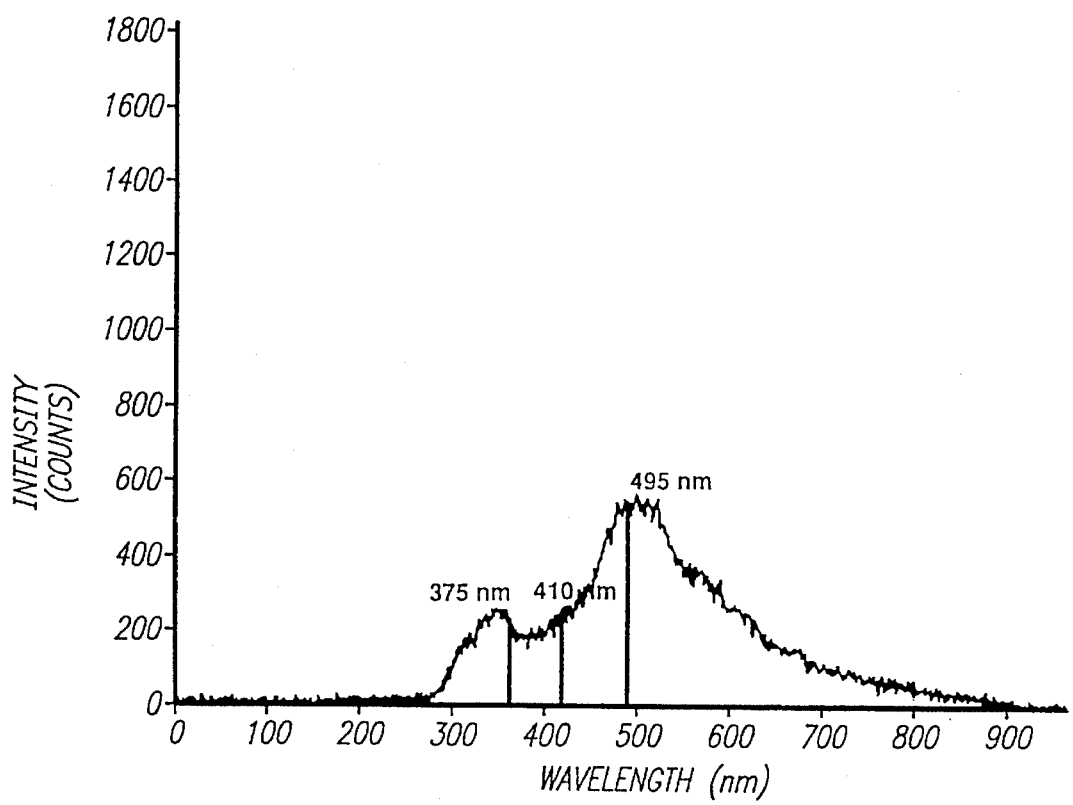
FIG. 9 is a graph of the intensity of fluorescence verses wavelength of a kidney having virtually no perfusion induced to fluoresce by laser light having a wavelength of about 308 nanometers.
Figure 10:
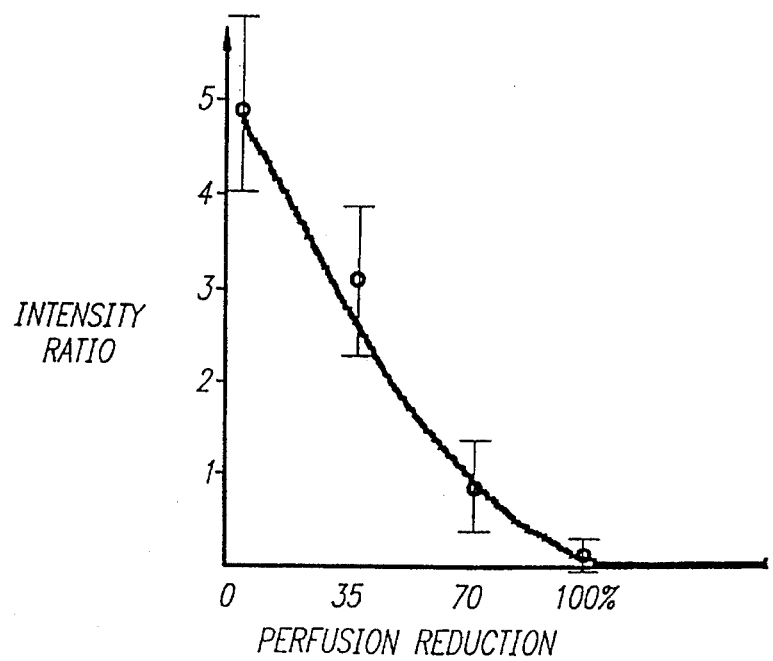
FIG. 10 is a graph of the intensity ratio $R_{perfusion}$ verses perfusion reduction.

The fluorescence spectrum shown in FIG. 7 is of a kidney having its perfusion or blood flow reduced to about 65% of full perfusion or normal blood flow (a 35% reduction) using an arterial embolectomy catheter. The fluorescence spectrum shown in FIG. 8 is of a kidney having its perfusion reduced to about 30% of full perfusion or normal blood flow (a 70% reduction). The fluorescence spectrum shown in FIG. 9 is of a kidney having virtually no perfusion or blood flow. The spectral profile between the graphs shown in FIGS. 7–9 are quite different. The blood perfusion can be determined by the ratio:

$$R_{PERFUSION} = (I^{ELASTIN} - I^{COLLAGEN})/(I^{NADH} - I^{COLLAGEN})$$

where $I^{ELASTIN}$ is the intensity of fluorescent light having a wavelength associated with Elastin, $I^{COLLAGEN}$ is the intensity of fluorescent light having a wavelength associated with collagen and $I^{NADH}$ is the intensity of fluorescent light having a wavelength associated with NADH. The statistical results of measurements on 60 rabbits is shown in FIG. 10. FIG. 10 shows that the kidney's blood perfusion is related to the ratio $R_{PERFUSION}$. Thus, induced fluorescence spectroscopy can give an accurate and rapid indication of the blood perfusion.

Figure 11:
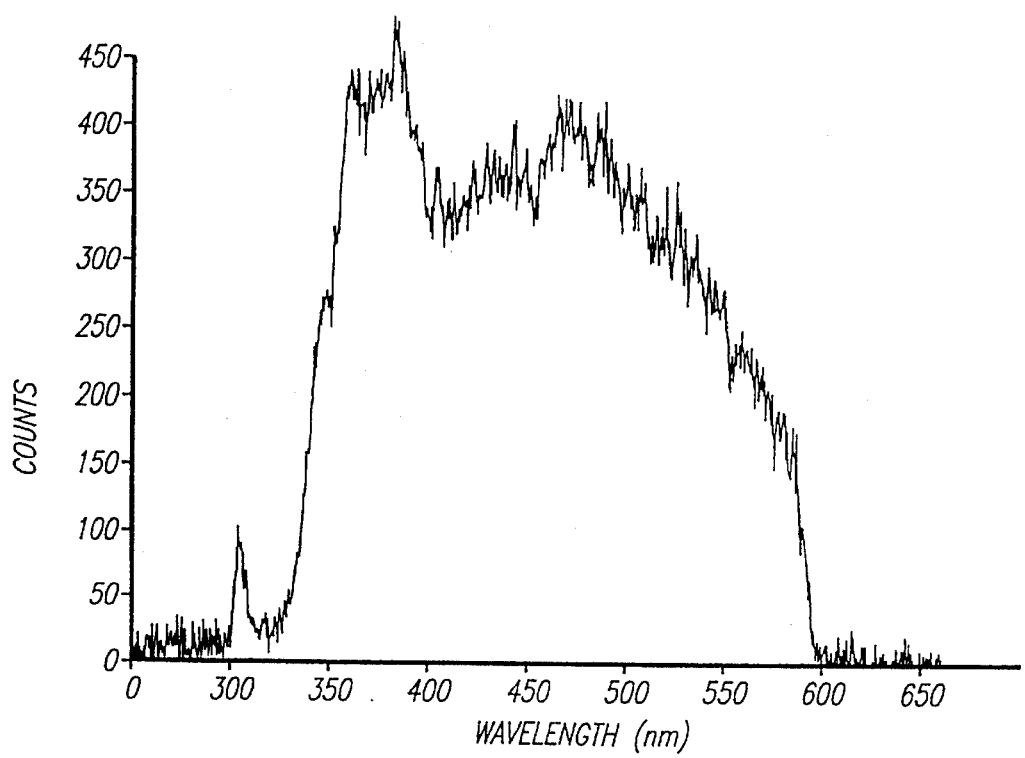
FIG. 11 is a graph of the intensity of fluorescence verses wavelength of a fully perfused liver induced to fluoresce by laser light having a wavelength of about 308 nanometers.
Figure 12:
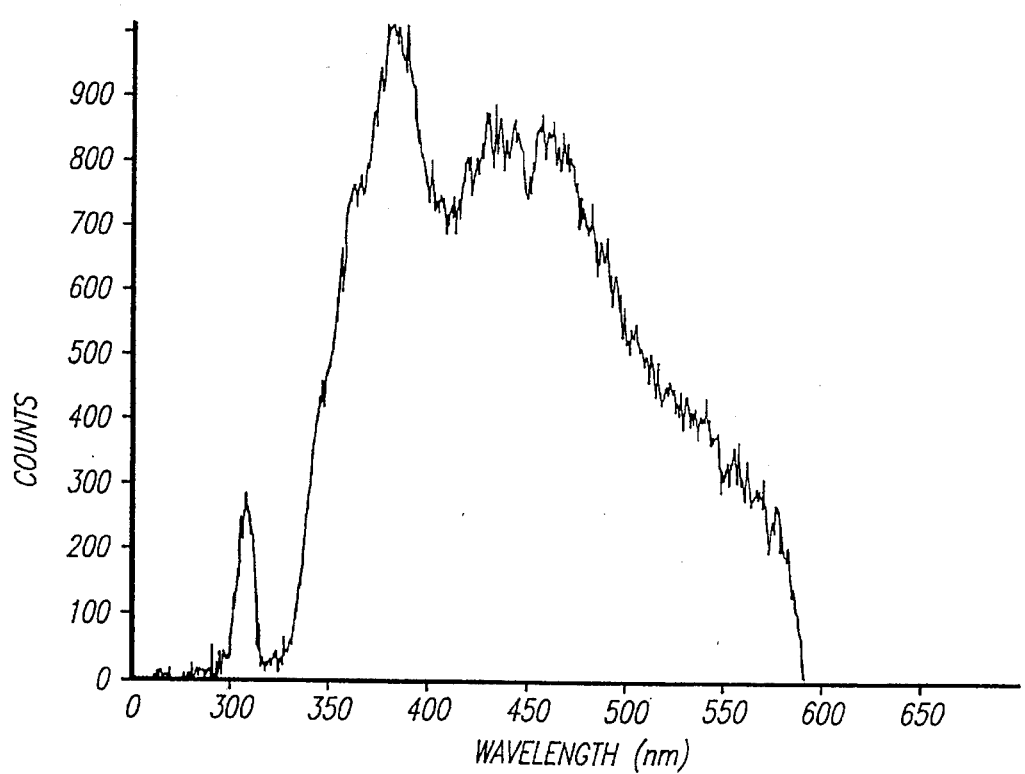
FIG. 12 is a graph of the intensity of fluorescence verses wavelength of a liver having virtually no perfusion for about 5 minutes induced to fluoresce by laser light having a wavelength of about 308 nanometers.

The induced fluorescence perfusion monitor is not limited to any specific single organ but may be used with almost any organ of the body and even with tissues in a tissue bed. As can be seen in FIGS. 11–12, similar spectral changes are observed in a liver between the fully perfused liver and a liver having no perfusion for 5 minutes as were observed for the kidney as discussed above. Thus, the monitor provides a simple, direct and practical device and related method for monitoring the physiology of almost any organ or tissue. For the purpose of defining the invention, the term organ includes the tissues of an organ, even if disassociated from the organ, such as tissues removed from an organ and cultivated in a tissue bed.

An alternative embodiment of the physiological monitor of the present invention is shown in FIG. 2A. This monitor uses a first fiber-optic waveguide 26 to transmit from a light source 14', the excitation light 16' to the organ 12 and to collect the return light 20' from the organ. The fiber-optic waveguide preferably has a core diameter of 400 microns. A first lens 28 focuses the excitation light 16' into one end of the first fiber-optic waveguide 26 and also collimates the collected return light that is emitted from the first fiber-optic waveguide. The collimated return light 20' passes through an ultraviolet mirror 30 and through a long pass optical filter 32. The long pass optical filter has a cutoff wavelength of 335 nanometers to filter reflected excitation light from the return light. The fluorescent light is focused into a second fiber-optic waveguide 34 by a second lens 36. This second fiber-optic waveguide 34 transmits the return light to the sensor 18' which includes a spectrograph 38. At the entrance of the spectrograph is a slit having a width of 150 micrometers. The slit is followed by a diffraction grating having 100 grates per millimeter that resolves the return light along an axis. A position along the axis corresponds to a wavelength of the return light.

Along the axis is positioned a detector 40, preferably a 1024-element charge-coupled device array. In the preferred embodiment, the detector is a 1024 element charge-coupled device array, part number EG&G 1422G. Each element of the detector array corresponds to a narrow spectral wavelength of the return light. The detector array provides an analog signal that is converted into a digital signal for analysis and processing by a suitable optical multichannel analyzer 22'. The digital signal contains data representing the intensity of light received within a plurality of narrow spectral wavelength bands. The data may be displayed on the screen of an optical-multichannel analyzer or saved on a data disk. A suitable system which includes both a detector and a multichannel analyzer is an OMA® 4 available from EG&G Princeton Applied Research of Princeton, N.J.

In an alternative embodiment of the present invention, the sensor 18' may include an aberration corrected wavelength division multiplexer (WDM) and a 512×512 pixel charged-coupled device (CCD) array. The fiber 46 which transmits and couples the return light into an f/2, 15 centimeter focal length aberration corrected WDM and the 512×512 pixel CCD array. The WDM's grating will be set at a fixed angle covering a 350 nanometer (between 300 and 650 nanometers) spectral range. The light exposure (light intensity x exposure time) for each pixel is digitized on a linear scale from 0 to $2^{14}$ (16,384). The array may be a liquid nitrogen cooled array which results in a substantial reduction of background noise signals. In addition, since the background noise signals are almost uniformly distributed across the array, the average noise signal may be subtracted from the fluorescence signal from each detector element of the array. A suitable sensor is the 1530-CUV cryogenically cooled CCD detector available from EG&G Princeton Applied Research of Princeton, N.J.

In another alternative embodiment, the sensor 18' may include a photodetector (PD) array having a built-in thermoelectric cooler (TEC). The TEC cooled array detector operates with lower noise levels than room temperature array detectors. A suitable TEC cooled array is the 1530-PUV thermoelectrically cooled CCD detector available from EG&G Princeton Applied Research of Princeton, N.J.

In an alternative embodiment of the invention, the processor 22 may include an artificial neural network as shown in FIG. 13. The artificial neural network consists of layers of interconnected processors (neurons) 50. The spectral data from the sensor 18 is input at input neuron layer 52. Preferably, each of the wavelengths discussed above is divided into 10 small bands or windows. The input neuron layer has sufficient inputs to receive the data for each of the wavelengths of interest. The neural network performs a nonlinear transformation on the input data and produces its result at the output neuron layer 54. Neural network has great flexibility in that it can be taught to transform the spectral data (input neuron layer) into an output (output neuron layer) that automatically and uniquely identifies the constituents of the organ with extremely high sensitivity (one to two orders higher than the conventional detection limit), high speed (a fraction of a second for identifying one spectrum), and high reliability (confidence level being indicated by the neural network output). The software implementing the neuron network is preferably, but not necessarily, the substance identification "Neural Network" software package from Physical Optics Corporation of Torrance, Calif. The neural network operations and decision making may be performed on an IBM compatible personal computer.

Figure 2B:
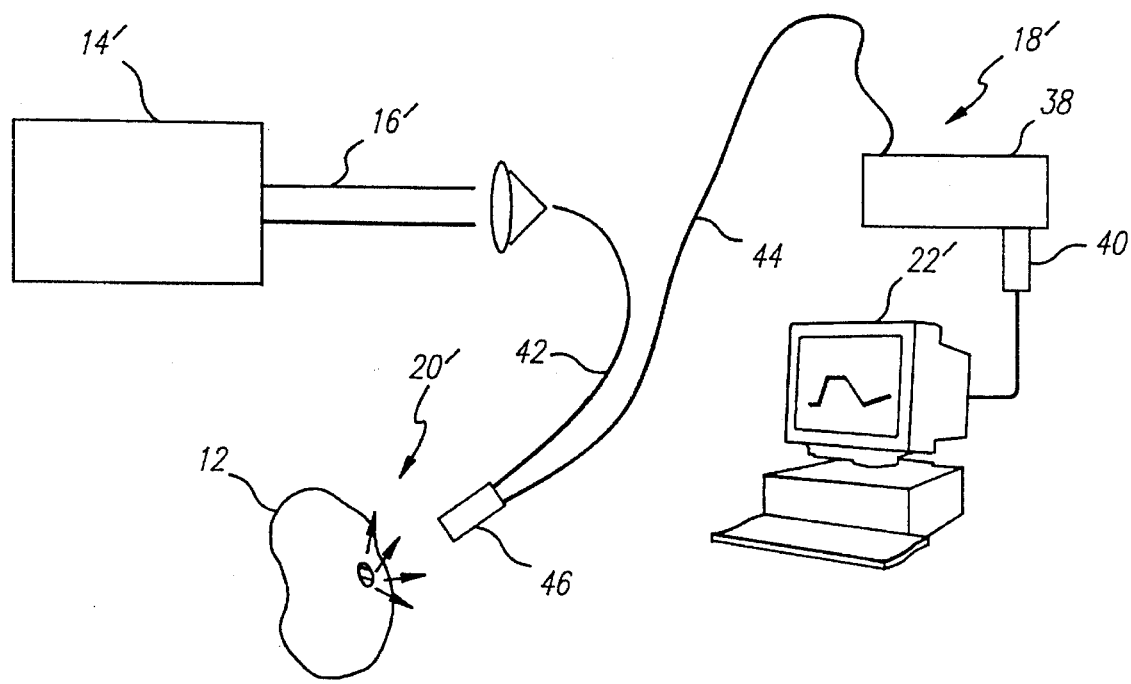

In another aspect of the invention shown in FIG. 2B, the separate fiber-optic waveguides are used for transmitting the excitation light and the return light. One fiber-optic waveguide 42 transmits the excitation light 16' from the light source 14 to the organ 12 and the other fiber-optic waveguide 44 collects the return light 20' from the organ and transmits it to the sensor 18'. The optical fibers may be integrated into a probe for ease of use. If the probe is configured within a narrow shaft of hypodermic needle, the physiological properties within the organ can be monitored. In addition, each of the fiber-optic waveguides 42 and 44 may be a single optical fiber or a bundle of several optical fibers.

From the foregoing, it will be appreciated that the physiological monitor of the present invention can provide almost instantaneous monitoring of an organ's pH and oxygenation at a specific portion of an organ in a patient without drawing blood from the patient's body or using similar techniques which give only a general indication of the condition of the patient's entire body. The physiology monitor monitors the induced fluorescence of the organ's metabolic and structural constituents directly giving a direct determination of the organ's chemistry without requiring complicated optical reference beam optics. The fiber-optic waveguides simplify the delivery of the excitation light to the organ and the collection of the return light from the organ.

Although the foregoing discloses preferred embodiments of the present invention, it is understood that those skilled in the art may make various changes to the preferred embodiments shown without departing from the scope of the invention. The invention is defined only by the following claims.

We claim:

1. Apparatus for determining a pre-existing physiological property of an organ having constituents including NADH and collagen, comprising:

a light source emits excitation light that is directed at an organ to produce return light from the organ, such return light including fluorescent light produced by any constituents present in the organ;

a sensor, responsive to the return light, that monitoring the return light and generates a first signal indicative of the intensity of return light within a first wavelength band associated with the fluorescence of NADH and generates a second signal indicative of the intensity of return light within a second wavelength band associated with the fluorescence of collagen; and a processor associated with the sensor processes the first and second signals and produces an output signal, based on the first and second signals, that represents the physiological property.

2. Apparatus for determining a pre-existing physiological property of an organ as defined in claim 1, wherein the output signal produced by the processor represents the pH of the organ.

3. Apparatus for determining a pre-existing physiological property of an organ as defined in claim 1, wherein:

the excitation light produced by the light source has a wavelength between about 250 nanometers and about 450 nanometers;

the first wavelength band is centered around a wavelength that is about 190 nanometers longer than the wavelength of the excitation wavelength; and the second wavelength band is centered around a wavelength that is about 100 nanometers longer than the wavelength of the excitation wavelength; and the output signal produced by the processor represents the acidity or alkalinity of the organ.

4. Apparatus for determining a pre-existing physiological property of an organ as defined in claim 3, wherein:

the excitation light produced by the light source has a wavelength centered at about 308 nanometers;

the first wavelength band is between about 485 and 505 nanometers; and the second wavelength band is between about 400 and 420 nanometers.

5. Apparatus for determining a pre-existing physiological property of an organ as defined in claim 1, wherein:

the excitation light produced by the light source has a wavelength centered at about 308 nanometers;

the first wavelength band is centered at about 495 nanometers;

the second wavelength band is centered at about 410 nanometers; and the output signal produced by the processor represents the acidity or alkalinity of the organ.

6. Apparatus for determining a pre-existing physiological property of an organ as defined in claim 1, wherein the processor produces the output signal in accordance with a ratio defined by the formula:

$$R_{pH} = I^{NADH}/I^{COLLAGEN}$$

where $R_{pH}$ is a ratio that represents the acidity or alkalinity of the organ, $I^{NADH}$ is the intensity of light within the first wavelength band, and $I^{COLLAGEN}$ is the intensity of light within the second wavelength band.

7. Apparatus for determining a pre-existing physiological property of an organ as defined in claim 1, wherein:

the constituents further include elastin;

the sensor generates a third signal indicative of the intensity of return light within a third wavelength band associated with the fluorescence of elastin; and the processor further receives the third signal from the sensor and processes the first, second and third signals such that the output signal is based also on the third signal and represents the blood perfusion of the organ.

8. Apparatus for determining a pre-existing physiological property of an organ as defined in claim 7, wherein:

the excitation light produced by the light source has a wavelength between about 250 nanometers and about 450 nanometers;

the first wavelength band is centered around a wavelength that is about 190 nanometers longer than the wavelength of the excitation wavelength;

the second wavelength band is centered around a wavelength that is about 100 nanometers longer than the wavelength of the excitation wavelength; and the third wavelength band is centered around a wavelength that is about 70 nanometers longer than the wavelength of the excitation wavelength.

9. Apparatus for determining a pre-existing physiological property of an organ as defined in claim 7, wherein:

the excitation light produced by the light source has a wavelength centered at about 308 nanometers;

the first wavelength band is between about 485 and 505 nanometers;

the second wavelength band is between about 400 and 420 nanometers; and the third wavelength band is between about 365 and 385 nanometers.

10. Apparatus for determining a pre-existing physiological property of an organ as defined in claim 7, wherein:

the excitation light produced by the light source has a wavelength centered at about 308 nanometers;

the first wavelength band is centered at about 495 nanometers;

the second wavelength band is centered at about 410 nanometers; and the third wavelength band is centered at about 375 nanometers.

11. Apparatus for determining a pre-existing physiological property of an organ as defined in claim 7, wherein the processor produces the output signal in accordance with a ratio defined by the formula:

$$R_{PERFUSION} = (I^{ELASTIN} - I^{COLLAGEN})/(I_{NADH} - I^{COLLAGEN})$$

where $R_{PERFUSION}$ is a ratio that represents the blood perfusion of the organ, $I^{NADH}$ is the intensity of light within the first wavelength band, $I^{COLLAGEN}$ is the intensity of light within the second wavelength band, and $I^{ELASTIN}$ is the intensity of light within the third wavelength band.

12. Apparatus for determining a pre-existing physiological property of an organ as defined in claim 1, further including a waveguide, associated with the light source, that transmitts the excitation light from the light source to the organ and that transmitts the return light from the organ to the sensor.

13. Apparatus for determining a pre-existing physiological property of an organ as defined in claim 12, and further comprising a probe for housing the waveguide.

14. Apparatus for determining a pre-existing physiological property of an organ as defined in claim 1, further comprising:

a first fiber-optic waveguide, associated with the light source, that transmitts the excitation light from the light source to the organ; and a second fiber-optic waveguide, associated with the sensor, that collects the return light and transmitts it from the organ to the sensor.

15. Apparatus for determining a pre-existing physiological property of an organ as defined in claim 1, further including:

a first fiber-optic waveguide, associated with the light source, that transmitts the excitation light from the light source to the organ and that collects the return light from the organ;

a second fiber-optic waveguide, associated with the sensor, for transmitting the return light to the sensor; and means for transmitting the return light from the first waveguide to the second waveguide, the means including a lens.

16. Apparatus for determining a pre-existing physiological property of an organ as defined in claim 1, wherein the sensor includes:

a first detector that detects the return light within the first wavelength band and generate the first signal; and a second detector that detects the return light within the second wavelength band and generate the second signal.

17. Apparatus for determining a pre-existing physiological property of an organ as defined in claim 1, wherein the sensor includes:

a spectrograph having an array of detectors, the spectrograph resolving the return light such that each detector of the array detects a different spectral wavelength of the return light and generates a separate electrical signal representing the intensity of light in its wavelength; and an optical analyzer, associated with the spectrograph, that analyzes the plurality of electrical signals received from the spectrograph and generates the first and second signals.

18. Apparatus for determining a pre-existing physiological property of an organ as defined in claim 1, wherein the sensor comprises:

a dichroic filter, within an optical path of the return light, that rejects return light having a wavelength equal to the wavelength of the excitation light and transmits the return light within the first and second wavelength bands;

a stop having a slit aperture, wherein a portion of the return light that is transmitted through the dichroic filter passes through the slit;

a grating that spreads the return light that passes through the slit such that the return light is spread along an axis by a distance proportional to the wavelength of the return light; and first and second electro-optical detectors that generate the first and second electrical signals, respectively, the first electro-optical detector located along the axis at a distance corresponding to the first wavelength band and the second electro-optical detector located along the axis at a distance corresponding to the second wavelength band.

19. Apparatus for determining a pre-existing physiological property of an organ as defined in claim 1, wherein the processor includes an artificial neural network.

20. A method of determining a pre-existing physiological property of an organ having constituents including NADH and collagen comprising:

directing excitation light at the organ to cause the organ to produce return light, such return light including fluorescent light produced by constituents present in the organ;

monitoring the return light and generating first and second signals, the first signal indicative of the intensity of the return light within a first wavelength band associated with the fluorescence of NADH and the second signal indicative of the intensity of return light within a second wavelength band associated with the fluorescence of collagen; and processing the first and second signals to produce an output signal, based on the first and second signals, that represents the physiological property of the organ.

21. A method for determining a pre-existing physiological property of an organ as defined in claim 20, wherein the output signal produced by the processor represents the pH of the organ.

22. A method of determining a pre-existing physiological property of an organ as defined in claim 20, wherein:

the excitation light used in the step of directing has a wavelength between about 250 nanometers and about 450 nanometers;

the first wavelength band used in the step of monitoring is about 190 nanometers longer than the wavelength of the excitation wavelength; and the second wavelength band used in step of monitoring is about 100 nanometers longer than the wavelength of the excitation wavelength; and the outside signal produced in the step of processing represents the acidity or alkalinity of the organ.

23. A method of determining a pre-existing physiological property of an organ as defined in claim 20, wherein:

the excitation light used in the step of directing has a wavelength centered at about 308 nanometers;

the first wavelength band used in the step of monitoring is between about 485 and 505 nanometers; and the second wavelength band used in the step of monitoring is between about 400 and 420 nanometers.

24. A method of determining a pre-existing physiological property of an organ as defined in claim 20, wherein:

the excitation light used in the step of directing has a wavelength centered at about 308 nanometers;

the first wavelength band used in the step of monitoring is centered at about 495 nanometers;

the second wavelength band used in the step of monitoring is centered at about 410 nanometers; and the output signal produced in the step of processing represents the acidity or alkalinity of the organ.

25. A method of determining a pre-existing physiological property of an organ as defined in claim 20, wherein the step of processing includes the step of determining a ratio defined by the formula:

$$R_{pH} = I^{NADH} / I^{COLLAGEN}$$

where $R_{pH}$ is a ratio that represents the acidity or alkalinity of the organ, $I^{NADH}$ is the intensity of light within the first wavelength band, and $I^{COLLAGEN}$ is the intensity of light within the second wavelength band.

26. A method of determining a pre-existing physiological property of an organ as defined in claim 20, wherein:

the pre-existing physiological property is the perfusion of the organ and the constituents further include elastin;

the step of monitoring further comprises the step of generating a third signal indicative of the intensity of return light within a third wavelength band associated with the fluorescence of elastin; and the step of processing includes processing the first, second, and third signals to produce an output signal that represents the perfusion of the organ.

27. A method of determining a pre-existing physiological property of an organ as defined in claim 26, wherein:

the excitation light used in the step of directing has a wavelength between about 250 nanometers and about 450 nanometers;

the first wavelength band used in step of monitoring is about 190 nanometers longer than the wavelength of the excitation wavelength;

the second wavelength band used in step of monitoring is about 100 nanometers longer than the wavelength of the excitation wavelength; and the third wavelength band used in step of monitoring is about 70 nanometers longer than the wavelength of the excitation wavelength.

28. A method of determining a pre-existing physiological property of an organ as defined in claim 26, wherein:

the excitation light used in the step of directing has a wavelength centered at about 308 nanometers;

the first wavelength band used in step of monitoring is between about 485 and 505 nanometers;

the second wavelength band used in step of monitoring is between about 400 and 420 nanometers; and the third wavelength band used in step of monitoring is between about 365 and 385 nanometers.

29. A method of determining a pre-existing physiological property of an organ as defined in claim 26, wherein:

the excitation light used in the step of directing has a wavelength centered at about 308 nanometers;

the first wavelength band used in step of monitoring is centered at about 495 nanometers;

the second wavelength band used in step of monitoring is centered at about 410 nanometers; and the third wavelength band used in step of monitoring is centered at about 375 nanometers.

30. A method of determining a pre-existing physiological property of an organ as defined in claim 26, wherein the step of processing includes the step of causing the output signal to assume a value in accordance with a ratio defined by the formula:

$$R_{PERFUSION} = (I^{ELASTIN} - I^{COLLAGEN}) / (I_{NADH} - I^{COLLAGEN})$$

where $R_{PERFUSION}$ is a ratio that represents the blood perfusion of the organ, $I^{NADH}$ is the intensity of light within the first wavelength band, $I^{COLLAGEN}$ is the intensity of light within the second wavelength band, and $I^{ELASTIN}$ is the intensity of light within the third wavelength band.

31. A method of determining a pre-existing physiological property of an organ as defined in claim 20, wherein the step of directing excitation light at an organ further comprises the step of guiding the excitation light from the light source to the organ.

32. A method of determining a pre-existing physiological property of an organ as defined in claim 20, wherein the step of monitoring the return light further comprises the step of guiding the return light from the organ to the sensor.

33. A method of determining a pre-existing physiological property of an organ as defined in claim 32, wherein the step of monitoring the return light further comprises the step of resolving the return light into its different spectral wavelengths to detect the light within the respective first and second wavelength bands.

34. Apparatus for determining the acidity or alkalinity of tissues of an organ, the tissues having constituents including NADH and collagen, comprising:

a light source that emits excitation light;

a first fiber-optic waveguide that transmits the excitation light from the light source to the tissues to cause the tissues to produce return light, such return light including fluorescent light produced by any compounds present in the tissues;

a second fiber-optic waveguide that transmits the return light from the tissues;

a sensor, associated with the second waveguide, for monitoring the return light, wherein the sensor generates a first signal indicative of the intensity of return light within a first wavelength band associated with the fluorescence of NADH and generates a second signal indicative of the intensity of return light within a second wavelength band associated with the fluorescence of collagen; and a processor that processes the first and second signals and produces an output signal that represents the acidity or alkalinity of the tissues.

35. Apparatus for determining the perfusion of the tissues of an organ, the tissues having constituents including NADH, collagen and elastin, comprising:

a light source that emits excitation light;

a first fiber-optic waveguide that transmits the excitation light from the light source to the tissues to cause the tissues to produce return light, such return light including fluorescent light produced by any compounds present in the tissues;

a second fiber-optic waveguide that transmits the return light from the tissues;

a sensor, associated with the waveguide, for monitoring the return light; wherein the sensor generates a first signal indicative of the intensity of return light within a first wavelength band associated with the fluorescence of NADH, generates a second signal indicative of the intensity of return light within a second wavelength band associated with the fluorescence of collagen, and generates a third signal indicative of the intensity of return light within a third wavelength band associated with the fluorescence of elastin; and a processor that processes the first, second, and third signals and produce an output signal that represents the blood perfusion of the tissues.

36. Apparatus for determining a pre-existing physiological property of an organ's tissues which include metabolic and structural constituents, comprising:

a light source that emits excitation light;

a first fiber-optic waveguide that transmits the excitation light from the light source to the tissues of an organ to cause the tissues to produce return light, such return light including fluorescent light produced by any compounds present in the tissues;

a second fiber-optic waveguide that transmits the return light from the tissues;

a sensor, responsive to the return light transmitted by the second waveguide, wherein the sensor monitors the return light and generates a first signal indicative of the intensity of return light within a first wavelength band associated with the fluorescence of a metabolic constituent, and generates a second signal indicative of the intensity of return light within a second wavelength band associated with the fluorescence of a structural constituent; and a processor that processes the first and second signals and produces an output signal that represents the physiological property.

37. Apparatus for determining a pre-existing physiological property of an organ having constituents including NADH and collagen, comprising:

a light source that emits excitation light which is directed at an organ to produce return light from the organ, such return light including fluorescent light produced by any constituents present in the organ;

a sensor having at least one output terminal for transmitting signals produced by the sensor in response to the return light, wherein the sensor monitors the return light and generates a first signal indicative of the intensity of return light within a first wavelength band associated with the fluorescence of NADH and generates a second signal indicative of the intensity of return light within a second wavelength band associated with the fluorescence of collagen; and a processor having at least one input terminal and an output terminal, wherein the processor receives the first and second signals from the sensor using the at least one input terminal, processes the first and second signals, and produces an output signal at the output terminal, that represents the physiological property.

* * * * *

UNITED STATES PATENT AND TRADEMARK OFFICE
CERTIFICATE OF CORRECTION

PATENT NO. : 5,456,252

DATED : October 10, 1995

INVENTOR(S) : Sandor G. Vari, Theodore Papazoglou & Warren S. Grundfest

It is certified that error appears in the above-identified patent and that said Letters Patent are hereby corrected as shown below:

In column 8, line 15, after "source" add the word --that--.
In column 8, line 19, change the word "monitoring" to --monitors--.
In column 8, line 26, after "sensor" add the word --that--.
In column 9, line 61, change subscript "NADH-" to superscript --NADH- --.
In column 10, line 5, change "transmitts" to --transmits--.
In column 10, line 6, change "transmitts" to --transmits--.
In column 10, line 15, change "transmitts" to --transmits--.
In column 10, line 18, change "transmitts" to --transmits--.
In column 10, line 24, change "transmitts" to --transmits--.
In column 12, line 64, change subscript "NADH-" to superscript --NADH- --.
In column 14, line 7, change "produce" to --produces--.

Signed and Sealed this

Fourth Day of June, 1996

*Attest:*

BRUCE LEHMAN

*Attesting Officer*   Commissioner of Patents and Trademarks